United States Patent
Reuter et al.

(10) Patent No.: US 10,653,151 B2
(45) Date of Patent: May 19, 2020

(54) COMPOSITION AND METHOD FOR REDUCING FUNGAL INFECTIONS IN CROPS

(71) Applicant: Phibro Animal Health Corporation, Teaneck, NJ (US)

(72) Inventors: Christopher J. Reuter, Parrish, FL (US); Steven J. MacKenzie, Sarasota, FL (US)

(73) Assignee: Phibro Animal Health Corporation, Teaneck, NJ (US)

( * ) Notice: Subject to any disclaimer, the term of this patent is extended or adjusted under 35 U.S.C. 154(b) by 0 days.

(21) Appl. No.: 15/886,124

(22) Filed: Feb. 1, 2018

(65) Prior Publication Data

US 2019/0230935 A1    Aug. 1, 2019

(51) Int. Cl.
*A01N 63/00*   (2020.01)
*C12R 1/07*    (2006.01)
*C12N 1/20*    (2006.01)

(52) U.S. Cl.
CPC .............. *A01N 63/00* (2013.01); *C12N 1/20* (2013.01); *C12R 1/07* (2013.01)

(58) Field of Classification Search
CPC .................................................... A01N 63/00
See application file for complete search history.

(56) References Cited

U.S. PATENT DOCUMENTS

2015/0257400 A1   9/2015 Reuter et al.
2015/0258150 A1   9/2015 Reuter et al.

FOREIGN PATENT DOCUMENTS

CN   107338202 A   11/2017

OTHER PUBLICATIONS

Zehnder et al. BioControl, 2000, 45:127-137.*
Ji et al. Mycobiology, 2013, 41(4):234-242.*
Kloepper et al. International J of Poultry Science, 2004, 3(5):361-364.*
International Search Report and Written Opinion dated May 16, 2019, Form PCT/ISA/220, (11 pages).
Khan, N. et al., Combating Fusarium Infection Using Bacillus-Based Antimicrobials, Microorganisms, Nov. 22, 2017, vol. 5, 75 pp. 1-13 (13 pages).
Yuan, J. et al., Antifungal Activity of *Bacillus amyloliquefaciens* NJN-6 Volatile Compounds against *Fusarium oxysporum* f. sp. Cubense, Applied and Environmental Microbiology, Aug. 2012, vol. 78, No. 16, pp. 5942-5944 (3 pages).

* cited by examiner

*Primary Examiner* — Bin Shen
(74) *Attorney, Agent, or Firm* — Klarquist Sparkman, LLP

(57) ABSTRACT

A composition useful for application to plants, seeds or soil to inhibit fungal infections comprises a protein source inoculated with from $5\times10^7$ cfu to $5\times10^9$ cfu of a *Bacillus amyloliquefaciens* strain per gram of the protein source.

10 Claims, 5 Drawing Sheets

Effect of TSB fermentation medium from different bacterial strains on Fusarium conidia germination % Germination Cont (-) untreated with any bacterial strain or germination medium
Cont (+) treated with germination medium
Treatments with a strain ID were treated with bacteria broth and conidia germination medium
Bars marked with a * are statistically reduced relative to Cont (+) at $p \leq 0.05$

FIG. 1

Effect of TSB fermentation medium from different bacterial strains on Fusarium conidia numbers Cont (-) untreated with any bacterial strain or germination medium
Cont (+) treated with germination medium
Treatments with a strain ID were treated with bacteria broth and conidia germination medium
Bars marked with a * are statistically reduced relative to Cont (-) at $p \leq 0.05$

FIG. 2

Effect of B. amyloliquefaciens without organic supplement on Fusarium in soil

[Bar chart: cfu/g Fusarium recovered from soil vs cfu/g B. amyloliquefaciens added to soil. Values approximately: 0 → 5.4E+04; 5e5 → 6.8E+04; 5e6 → 7.0E+04]

Each treatment was repeated 3 times. B. amyloliquefaciens at either concentration did not affect recovery of Fusarium

FIG. 4

# COMPOSITION AND METHOD FOR REDUCING FUNGAL INFECTIONS IN CROPS

CROSS-REFERENCE TO RELATED APPLICATIONS

Not Applicable.

FIELD OF THE DISCLOSURE

This disclosure relates to methods and compositions for reducing or eliminating fungal infections of growing and/or harvested crops using non-pathogenic bacteria.

BACKGROUND OF THE DISCLOSURE

Members of the species Bacillus have been reported to be useful for preventing infections and/or promoting the growth of crops. For example, *Bacillus pumilus* strain QST2808, *Bacillus pumilus* strain GB34, *Bacillus Substilis* strain QST713, *Bacillus Subtilis* strain GB03, various strains of *Bacillus thuringiensis* and *Bacillus firmus*, and *Bacillus amyloliquefaciens* strain FZB42 have been used in commercially available biocontrol products.

While the known natural, non-pathogenic, biological fungicides have achieved some commercial success, there remains a need for safe and highly effective biological fungicides.

SUMMARY OF THE DISCLOSURE

This disclosure relates to a safe (non-toxic, non-pathogenic) biological fungicide composition containing a protein source inoculated with from $5 \times 10^7$ cfu to $5 \times 10^9$ cfu of a *Bacillus amyloliquefacias* strain per gram of the protein source. The combination of a protein source and a biocidal strain of a *Bacillus amyloliquefacies* has been found to be more effective at reducing and/or inhibiting fungal infections in crops than either component alone, providing an unexpected and synergistic improvement.

BRIEF DESCRIPTION OF THE DRAWINGS

FIG. 1 is a bar chart showing the inhibitory effect of fermentation medium effluent from different bacteria strains on *Fusarium oxysporum* conidia germination.

FIG. 2 is a bar chart showing the inhibitory effect of fermentation medium effluent from different bacteria strains on *Fusarium oxysporum* conidia numbers.

FIG. 4 is a bar chart showing that the addition of the *Bacillus amyloliquefaciens* strain alone, without the protein source, to soil in which a plant is grown does not effectively inhibit *Fusarium oxysporum*.

DETAILED DESCRIPTION OF THE DISCLOSED EMBODIMENTS

Figure 3:
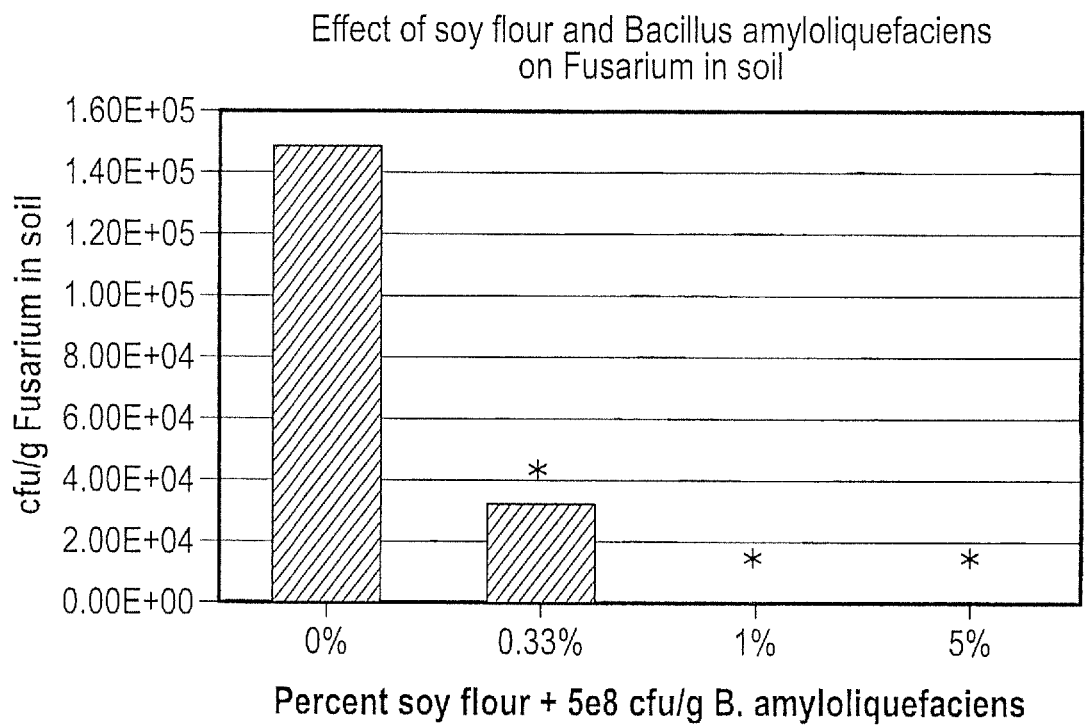
FIG. 3 is a bar chart showing the inhibitory effect of adding a composition containing a protein source inoculated with a strain of *Bacillus amyloliquefaciens* to a soil in which a plant is grown.

Based on experiments in which various *Bacillus* species were screened for their ability to promote growth of basil plants treated with a protein source selected from cotton seed meal, soybean flour and hydrolyzed feather meal, it was determined that the growth response to cotton seed meal and soybean flour was very poor regardless of the species of *Bacillus* and amount of *Bacillus* used. It was also determined that the growth response to hydrolyzed feather meal was good regardless of the amount or species of *Bacillus* used. This suggested to the inventors that the soybean flour and cotton seed meal was being consumed by bacteria and incorporated in the mass of the bacteria. The bacteria responsible for metabolizing the protein sources could be native bacteria, added bacteria (the protein source inoculant), or a combination of both inoculant and native bacteria. This suggested to the inventors that certain protein sources, such as soybean flour and cotton seed meal, could be used to supplement the growth of a biocontrol organism, such as a fungicidial bacteria.

Deposit of Biological Material

The following biological materials have been deposited under the terms of the Budapest Treaty with the American Type Culture Collection, 10801 University Boulevard, Manassas, Va., 20110, (ATCC) and given the following deposit designation numbers:

PTA-122189 - *Bacillus amyloliquefaciens* strain OBT-712 deposited on May 29, 2015; and PTA-124660 - *Bacillus amyloliquefaciens* strain OBT-730 deposited on Jan. 12, 2018.

The *Bacillus amyloliquefaciens* strains were deposited under conditions that assure that access to the bacteria will be available during the pendency of this patent application to one determined by the Commissioner of Patents and Trademarks to be entitled thereto under 37 C.F.R. § 1.14 and 35 U.S.C. § 122. The deposits represent substantially pure samples of each of the *Bacillus amyloliquefaciens* strains. The deposits are available as required by foreign patent laws in countries wherein counterparts of the subject application, or its progeny, are filed. All restrictions on the availability to the public of the material so deposited will be irrevocably removed upon the granting of a patent. However, it should be understood that the availability of a deposit does not constitute a license to practice the subject invention in derogation of patent rights granted by governmental action.

Based on separate experiments in which various *Bacillus* strains were screened for their ability to inhibit germination of conidia in water and their ability to lyse conidia in water, it was determined that the effluent from tryptic soy broth (TSB) media used for cultivating the various *Bacillus* strains tested typically contained secreted substances capable of inhibiting germination of conidia from *Fusarium oxysporum*. However, as shown in FIG. 1, there were exceptions, such as *B. pumilus* strain BP, which did not appreciably inhibit *Fusarium oxysporum*. Also, as shown in FIG. 1, *B. amyloliquefaciens* strains OBT 730 (deposited as ATCC Accession No. PTA-124660), and OBT 712 (deposited as ATCC Accession No. PTA-122189) were particularly effective at inhibiting *Fusarium* conidia germination.

FIG. 2 shows that the ability of effluents from strains OBT 730 and OBT 712 to lyse *Fusarium oxysporum* conidia were particularly good, with over 70% of the conidia disappearing. Among the remaining conidia, percent germination was much lower for the effluents from strains OBT 730 and OBT 712 than observed when conidia were treated with effluent from other cultures.

Strain OBT 712 is a stock strain sold in most *Bacillus*-based products sold by Osprey Biotechnics, Sarasota, Fla., and strain OBT 730 was isolated by Osprey Biotechnics from a soil sample.

Strain OBT 712 was selected for further analysis. Specifically, experiments were conducted to determine the ability of strain OBT 712 to reduce *Fusarium* conidia concentrations in soil, both with and without soybean flour. Soybean flour was inoculated with $5 \times 10^8$ cfu *B. amyloliquefaciens* strain OBT 712 per gram of soybean flour. The inoculated soybean flour was added to soil in amounts of zero, 0.33%, 1% and 5%, and *Fusarium oxysporum* conidia was added at $5 \times 10^5$ conidia per gram of soil. The addition of *B. amyloliquefaciens*-inoculated soybean flour very substantially reduced *Fusarium* that could be recovered from the soil, as shown in FIG. 3.

Figure 5:
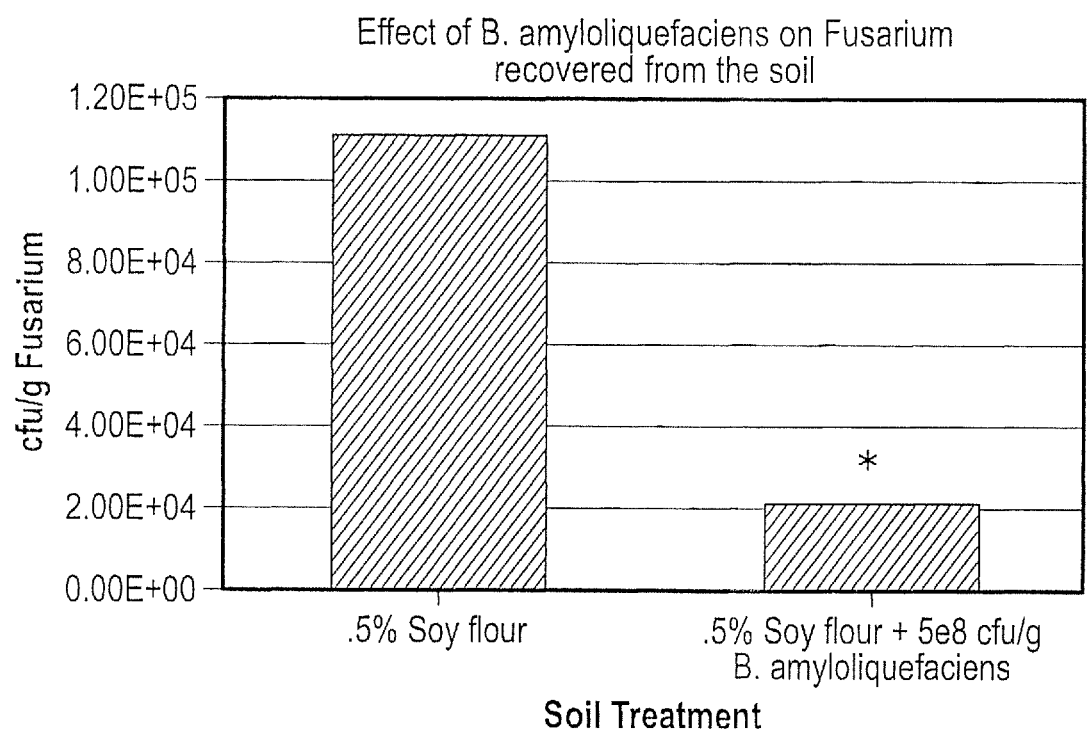
FIG. 5 is a bar chart showing that soybean flour inoculated with a strain of *Bacillus amyloliquefaciens* is much more effective than soybean flour alone at inhibiting *Fusarium oxysporum* in soil.

The inventors conducted several other studies to determine whether the OBT 712 strain could reduce *Fusarium* counts in the absence of soy flour and whether the effect on *Fusarium* was due to soy flour alone or if the bacteria was required. One percent soy flour inoculated with $5 \times 10^8$ cfu strain OBT 712 per gram of soybean flour would deliver $5 \times 10^6$ cfu strain OBT 712 per gram of soil. Neither this concentration nor $5 \times 10^5$ cfu strain OBT 712 per gram of soil appeared to appreciably affect *Fusarium* (FIG. 4). However, when compared to soy flour alone, soy flour plus strain OBT 712 reduced *Fusarium* recovery by approximately 80% (FIG. 5).

The inventors have concluded from the above experiments that a soil amendment comprising soy flour inoculated with *Bacillus amyloliquefaciens* can be used to reduce *Fusarium* infections in crops. Soy flour appears to have an advantage over other nitrogen sources tested. The amount of soy required to observe a beneficial effect on *Fusarium* recovery is much lower than other organic nitrogen supplies. At 0.5% soy flour, the nitrogen content of the potting soil is approximately 375 ppm. Typically one would want a nitrogen concentration in the 100-200 ppm range, but given that *B. amyloliquefaciens* is growing on the substrate and assimilating nitrogen it is conceivable that free nitrogen would be much lower than 200 ppm and that detrimental effects to the plant would not be observed.

Alternatively, fermentation broth in itself could make a suitable anti-fungal product. One could use routine experimentation to determine the percentage of the material that could be used as a fungicide. The secreted products that are likely responsible for the anti-fungal activity of the *B. amyloliquefaciens* strains are lipopeptides. Examples being iturin, surfactin, and fengycin. Genes encoding for enzymes required for the synthesis of these compounds are present in the strain OBT 712 genome. These peptides have been shown to be haemolytic and as a result have not been commercialized.

The compositions (inoculated protein sources and effluents from cultures) disclosed herein can be used to inhibit fungal infections in plants by applying the compositions to the plants, to seeds from which the plants are grown, or to soil in which the plants are grown. Soil concentrations generally refer to concentrations within soil that the roots of the plant contact. Application to seeds refers to incorporating the disclosed compositions in a seed covering. "Effluents," refer to filtered liquids obtained from media in which the disclosed bacteria are cultured.

The described embodiments are preferred and/or illustrated, but are not limiting. Various modifications are considered within the purview and scope of the appended claims.

What is claimed is:

1. A process, comprising applying to a seed, or to soil in which a plant is grown, a composition comprising a protein source selected from soybean flour or cotton seed meal and from $5 \times 10^7$ cfu to $5 \times 10^9$ cfu of a *Bacillus amyloliquefaciens* strain per gram of the protein source.

2. The process of claim 1, wherein the composition is added to the soil in which the plant is grown, such that the composition is present in the soil at an amount of from about 0.33% to about 5% of the mass of the soil.

3. The process of claim 1, wherein the *Bacillus amyloliquefaciens* strain has the identifying characteristics of a bacterium designated strain OBT 712, deposited as ATCC Accession No. PTA-122189.

4. The process of claim 1, wherein the *Bacillus amyloliquefaciens* strain has the identifying characteristics of a bacterium designated strain OBT 730, deposited as ATCC Accession No. PTA-124660.

5. The process of claim 1, wherein the plant is infected with a strain of *Fusarium oxysporum*.

6. A process, comprising applying to a plant, or to soil in which a plant is grown, effluent from a *Bacillus amyloliquefaciens* strain grown in a cultivation medium, the *Bacillus amyloliquefaciens* strain having the identifying characteristics of a bacterium designated strain OBT 712, deposited as ATCC Accession No. PTA-122189, wherein the cultivation medium is tryptic soy broth.

7. A process, comprising applying to a seed, or to soil in which a plant is grown, a composition comprising soybean flour and a *Bacillus amyloliquefaciens* strain having the identifying characteristics of a bacterium designated strain OBT 712, deposited as ATCC Accession No. PTA-122189 in an amount of from $5 \times 10^7$ cfu to $5 \times 10^9$ cfu *Bacillus amyloliquefaciens* per gram of soybean flour.

8. A process, comprising:
providing a composition comprising a protein source selected from soybean flour or cotton seed meal and from $5 \times 10^7$ cfu to $5 \times 10^9$ cfu of a *Bacillus amyloliquefaciens* strain per gram of the protein source; and
applying the composition to a seed or to soil.

9. The process of claim 8, wherein the composition is applied to the seed.

10. The process of claim 9, wherein the composition comprises soybean flour and a *Bacillus amyloliquefaciens* strain having the identifying characteristics of a bacterium designated strain OBT 712, deposited as ATCC Accession No. PTA-122189 in an amount of from $5 \times 10^7$ cfu to $5 \times 10^9$ cfu *Bacillus amyloliquefaciens* per gram of soybean flour.

* * * * *